United States Patent

Mizuno

[11] Patent Number: 6,067,153
[45] Date of Patent: *May 23, 2000

[54] PATTERN DEFECT INSPECTING APPARATUS

[75] Inventor: Fumio Mizuno, Tokorozawa, Japan

[73] Assignee: Hitachi, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/855,824

[22] Filed: May 12, 1997

[30] Foreign Application Priority Data

May 21, 1996 [JP] Japan ................................. 8-125591

[51] Int. Cl.⁷ .................................................. G06K 9/46
[52] U.S. Cl. .......................................... 356/237; 356/394
[58] Field of Search ..................... 356/237, 394, 356/431, 389

[56] References Cited

U.S. PATENT DOCUMENTS 5,576,833  11/1996  Miyoshi et al. .......................... 356/357

FOREIGN PATENT DOCUMENTS 27 00 252  3/1985  Germany .
34 27 981  2/1986  Germany .

Primary Examiner—Frank G. Font
Assistant Examiner—Reginald A. Ratliff
Attorney, Agent, or Firm—Kenyon & Kenyon

[57] ABSTRACT

A high-speed pattern defect inspecting apparatus with a high sensitivity and less erroneous detection. In the pattern defect inspecting apparatus, a wafer is scanned by an electron beam, secondary electron signal generated by the scanning is stored in an image memory, and the stored image is used to cause a display unit to be subjected to a brightness modulation. A reference pattern image previously stored in the image memory is compared with a detected wafer pattern image to find a difference between the both images, and the difference is detected as a defect in a wafer pattern. The wafer scanning of the electron beam is carried out only for an arbitrary specified part thereon.

33 Claims, 3 Drawing Sheets

OUT OF PATTERN AREA TO BE INSPECTED
PATTERN TO BE INSPECTED

WITHIN PATTERN AREA TO BE INSPECTED

PATTERN EDGE AREA

SAMPLE IMAGE

REFERENCE IMAGE

CONVEX DEFECT
CONCAVE DEFECT
DIFFERENCE IMAGE

SAMPLE IMAGE

SPECIFICATION RANGE

PORTIONS OUT OF SPECIFICATION RANGE

SAMPLE LINE PROFILE

REFERENCE LINE PROFILE

PORTIONS OUT OF SPECIFICATION RANGE

PATTERN DEFECT INSPECTING APPARATUS

BACKGROUND OF THE INVENTION

The present invention relates to pattern defect inspecting apparatus and more particularly, to a pattern defect inspecting apparatus which can suitably inspect a defect in a pattern in fabrication of semiconductor devices, image pick-up elements, display elements, etc.

Major examples of pattern defect inspecting apparatuses associated with the present invention include a scanning electron microscope (SEM), a laser scanning microscope, and a scanning inter-atomic force microscope. Explanation will be made in connection with an example of semiconductor fabrication as a typical application field. The SEM has been widely used in inspection of pattern defect. Thus explanation will be made in connection with the use of the SEM.

FIG. 1 is an arrangement of an SEM for explaining its basic principle, in which an electron beam is used as a probe to perform a raster scan on the entire surface of a field of view.

An electron beam 2 emitted from an electron gun 1 is accelerated, and converged through a condenser lens 3 and an objective lens 4, and then focused on a surface of a wafer 5 as an sample. Concurrently, the electron beam 2 is bent in its locus by a deflector 6 so that the beam two-dimensionally or one-dimensionally scans the entire surface of the wafer. Meanwhile, a part of the wafer, when subjected to an irradiation of the electron beam 2, emits secondary electrons. The secondary electrons are detected by a secondary electron detector 8 to be converted to an electric signal, the signal is converted by an A/D converter 9 to a digital signal and stored in an image memory 10. The stored signal is processed by an image processor 11 to be used for brightness modulation or Y modulation of a display unit 12. The display unit 12 is scanned similarly to the scanning of the electron beam 2 on the wafer, so that a sample image is formed on the display unit 12. When two-dimensional scanning and brightness modulation are carried out, an image appears on the display unit; whereas, when the Y modulation is carried out, a line profile is depicted on the display.

Here is an example of procedure of inspecting a pattern defect with use of the SEM.

A sheet of wafer 5 to be measured is extracted from a wafer cassette 13, and then subjected to a pre-aligning operation. The pre-alignment is to align the wafer direction with respect to an orientation flat or notch formed in the wafer as a reference. More in detail, after being subjected to the pre-alignment, the wafer 5 is fed into a sample chamber 14 kept in a vacuum and then placed on an X-Y stage 15 in the chamber. The wafer 5 placed on the X-Y stage 15 is aligned with use of an optical microscope 16 mounted in an upper part of the sample chamber 14. The alignment in this example is to correct a relationship between a positional coordinate system of the X-Y stage 15 and a pattern positional coordinate system of the wafer, for which end an alignment pattern formed on the wafer is used. More specifically, an image generated by the optical microscope 16 is converted by a CCD element or the like to an electric signal, converted by an A/D converter 17 to a digital signal, and then stored in the image memory 10. The stored signal is coupled to the display unit 12 via the image processor 11 so that the image of the optical microscope appears on the display unit 12. The image of the optical microscope magnified to a size about several hundred times the size of the alignment pattern is compared with a reference image of an alignment pattern previously registered, and the stage positional coordinate system is corrected so that its field of view exactly overlaps with the field of view of the reference image. After the alignment, a raster scan is carried out on the entire surface of a required inspection zone on the wafer using combination of the electron beam scan and stage movement to thereby form an SEM image. The formed SEM image is compared with the reference SEM image so that a difference between the images is detected as a pattern defect. Generally used as the reference SEM image is an SEM image of the same part in a chip or cell already inspected.

In this connection, control over the storing and reading operation of the image signal, the processing of the image signal, pattern matching, etc. is carried out under control of a computer/controller 18.

There is a reciprocal relationship between detection sensitivity for pattern defects and an inspection rate therefor. Both the detection sensitivity and inspection rate depend on pixel size (the number of pixels in the view field). When the pixel size is made small (when the number of pixels in the view field is increased), the pattern defect detection sensitivity can be made high but the inspection rate is decreased. That is, when a pattern defect is to be detected with a high sensitivity, its required inspection time is increased.

There is also a correlation between the pattern defect detection sensitivity and error detection frequency. The defect detection sensitivity is proportional to the resolution of the SEM. When the SEM resolution is increased in order to increase the defect detection sensitivity, a fine structure other than the pattern edge becomes also clear. The clear fine structure is frequently erroneously judged as a pattern edge, which leads to noise caused by the pattern defect (error detection factor). In other words, when the pattern defect is detected with a high sensitivity, the error detection rate is increased.

SUMMARY OF THE INVENTION

It is therefore an object of the present invention to provide a pattern defect inspecting apparatus which can suitably perform pattern defect inspection with a high sensitivity at a high rate while preventing increase of an error detection rate.

In accordance with the present invention, there is provided a pattern defect inspecting apparatus which scans a surface of a sample by means of a probe to inspect a defect in a pattern on the basis of information on the pattern imaged on the sample surface, and wherein the scanning of the probe on the sample is carried out for an arbitrarily specified area of the sample surface.

The scanning of the present invention is based on a so-called vector scan. For this reason, even when pixel size is made small, a scanning area of a fine structure is narrow, so that the number of pixels is not so large. That is, even when the pixel size is made small to detect a pattern defect with a high sensitivity, only a short inspection time is required. Further, since information on areas of the fine structure other than the specified area cannot be obtained, it can be avoided that the non-specified areas of the fine structure result in noise caused by pattern edge detection. That is, even when the resolution is made and a high pattern defect is detected with a high sensitivity, the error detection rate will not increase.

In accordance with the present invention, in this way, pinhole defects or island-like defects in the areas other than the specified area will not be detected. In addition, such defects will lead to a fatal defect in the element with a small probability and thus missing inspection will not involve a big disadvantage.

DETAILED DESCRIPTION

Figure 1:
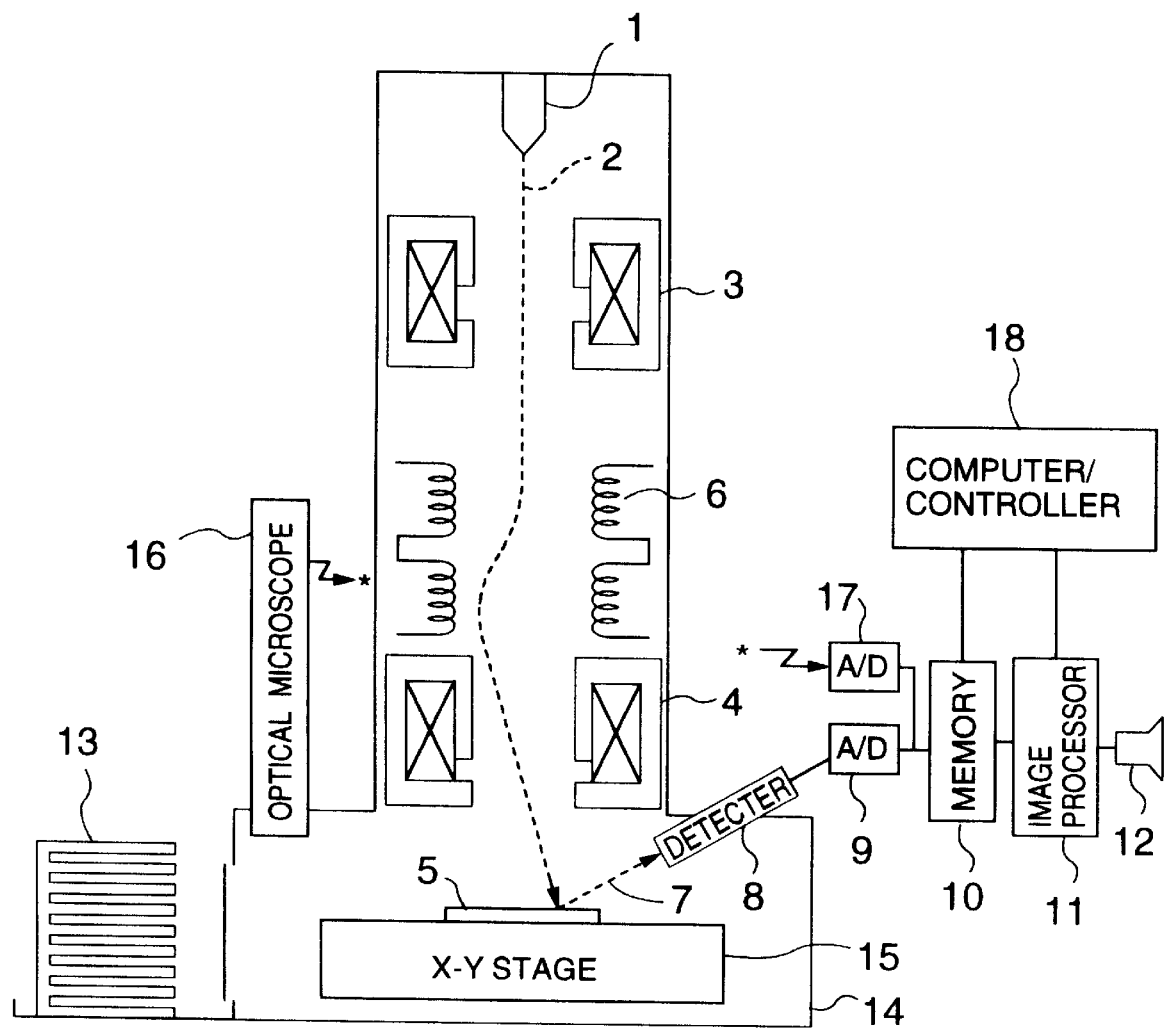
FIG. 1 is a conceptional view of a SEM for explaining the present invention and the prior art.

Hardware of a pattern defect inspecting apparatus of the present invention is the same as that of FIG. 1, and thus explanation thereof is omitted to avoid repetition.

Figure 2A:
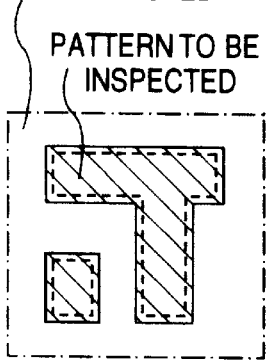
FIGS. 2A, 2B and 2C are diagrams for explaining the vector probe scan used in the present invention.
Figure 2B:
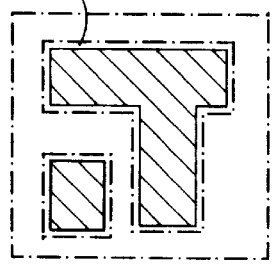
Figure 2C:
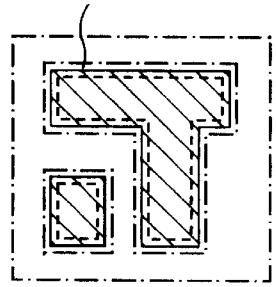

Different methods of performing vector scan on a specified pattern area are shown, in model form, by chain-dotted lines, e.g., in FIGS. 2A, 2B and 2C. More in detail:

(1) As shown in FIG. 2A, an electron beam is scanned on an area which is defined between an outside chain-dotted line and an inside chain-dotted line in FIG. 2A, that is, on an outer periphery of a pattern to be inspected, including a pattern edge. This method is valid when a line pattern is inspected or when such a convex defect as a residual resist or etched remainders is inspected.

(2) As shown in FIG. 2B, an electron beam is scanned on an area surrounded by a chain-dotted line in FIG. 2B, that is, on an inside area of a pattern to be inspected, including a pattern edge. This method is valid when a hole pattern is inspected or when such a concave defect as a defect caused by improperly narrow resist or missing of etching is inspected.

(3) As shown in FIG. 2C, an electron beam is scanned on a pattern edge area defined between a chain-dotted line located inside of a pattern to be inspected and a chain-dotted line located outside thereof. This method can also be applied to both of the above convex and concave defect inspections. When the methods of FIGS. 2A, 2B and 2C can be more effectively used in their combination for a part of the inspection pattern seemingly regarded as weak in the pattern formation. Any combination of the methods of FIGS. 2A, 2B and 2C may be employed in a single inspection work.

Figure 3A:
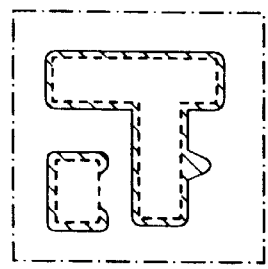
FIGS. 3A, 3B and 3C are diagrams for explaining an example of how to judge a pattern defect using the present invention.
Figure 3B:
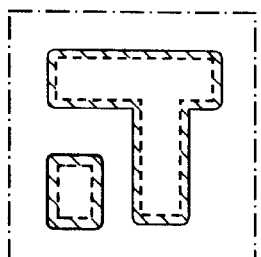
Figure 3C:
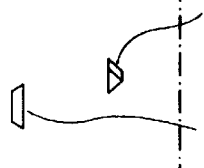

Ones of methods for judging a pattern defect are shown, in model form, e.g., in FIGS. 3A, 3B, 3C, 4A, 4B, 4C, 5A, 5B and 5C. More specifically:

(1) An SEM image (see FIG. 3A) is compared with a reference image (see FIG. 3B) previously registered, e.g., by the aforementioned pattern matching technique to detect a difference between the both images as a pattern defect (see FIG. 3C). The comparison with the reference image may be achieved by pattern shape collation or pattern edge matching.

Figure 4A:
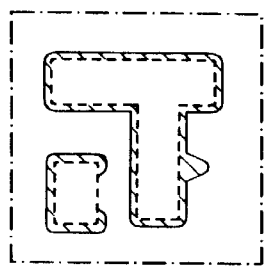
FIGS. 4A, 4B and 4C are diagrams for explaining another example of how to judge a pattern defect using the present invention.
Figure 4B:
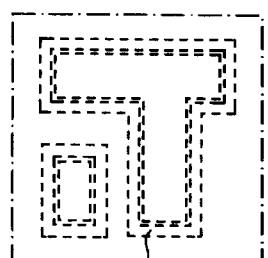
Figure 4C:
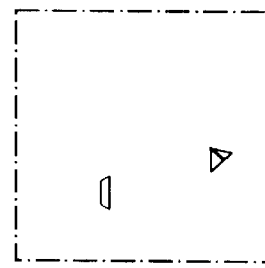

(2) When a pattern image within a SEM image (see FIG. 4A) is overlapped with a specification range (an area surrounded by dotted lines in FIG. 4B) defined by predetermined upper and lower limit lines to find a part not overlapped and when a non-overlapped part is found, the part is detected as a defect (see FIG. 4C).

(3) A sample line profile (see FIG. 5A) is compared with a reference line profile (defined by upper and lower dotted lines in FIG. 5B) previously registered, and a difference between the both profiles is detected as a pattern defect.

Figure 5A:
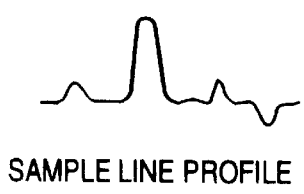
FIGS. 5A, 5B and 5C are diagrams for explaining a further example of how to judge a pattern defect using the present invention.
Figure 5B:
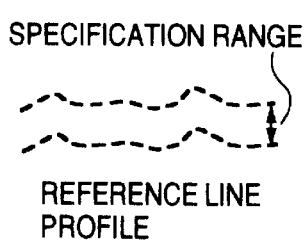
Figure 5C:
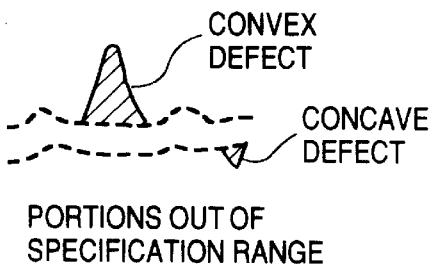

(4) A part of the sample line profile (see FIG. 5A) located outside of a predetermined specification range of the reference line profile (see FIG. 5B) is detected as a defect (see FIG. 5C).

When the above methods (3) and (4) are used as combined with the method of FIG. 2C for scanning the pattern edge with a single stroke of electron beam, high speed inspection can be effectively achieved. In either case, a plurality of reference images or specification ranges as upper and lower specification limits may be set.

In the judging operations of FIG. 3A, 3B, 3C, 4A, 4B, 4C, 5A, 5B and 5C, information about defect size and defect mode such as defect size, convex or concave defect can be obtained. It is also possible to add operational results classified according to the defect size and defect mode to the contents of the defect judgement. Even in the absence of a defect, the sample image may be different in its brightness or contrast between its chips or cells.

When image parameters such as brightness, saturation and contrast of the sample and reference images are arranged to be modified respectively independently, or when profile parameters such as amplitude and contrast of the sample and reference line profile are arranged to be modified respectively independently; relative accuracy can be improved.

Figure 6:
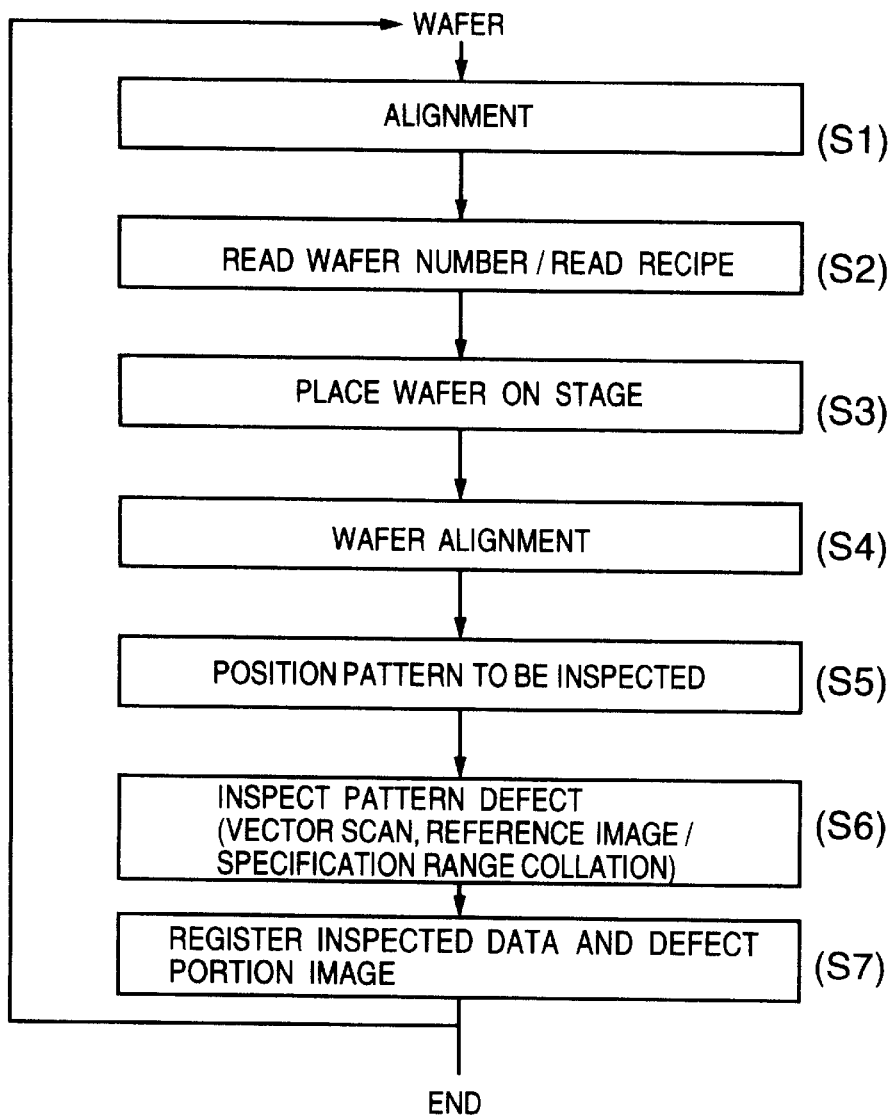
FIG. 6 shows an exemplary flowchart of pattern defect inspection according to the present invention.

Shown in FIG. 6 is an example of an operational procedure in the present invention.

The wafer 5 is extracted from the wafer cassette 13 and then subjected to a prealigning operation (step S1). After the prealignment, a wafer number formed on the wafer 5 is read out by a wafer number reader (not shown) (step S2). The wafer number is uniquely given to the wafer. A recipe of the wafer previously registered in the computer/controller 18 is read out based on the read-out wafer number as a key (step S2). Prescribed in the recipe are the inspection procedure and conditions of the wafer. The subsequent operations are carried out automatically or semiautomatically according to the recipe. After the recipe is read out, the wafer 5 is fed into the sample chamber 14 kept in a vacuum and then placed on the X-Y stage 15 (step S3). The wafer 5 placed on the stage is aligned with use of the optical microscope 16 mounted in the upper part of the sample chamber 14, and an alignment pattern formed on the wafer 5 (step S4). An image of the alignment pattern formed in the optical microscope is compared with a reference image of the alignment pattern previously stored in the image memory 10 as associated with the recipe, and a stage positional coordinate system is corrected so that its field of view is overlapped with a field of view of the reference image. After the alignment, a pattern formed on the wafer 5 to be inspected is accurately positioned with use of a positioning pattern formed on the wafer 5 (step S5). The positioning pattern is moved through a movement of the stage so as to be subjected to an electron beam, whereby its image is formed. The image of the positioning pattern, like the aligning operation, is compared with a reference image of the positioning pattern previously registered in the image memory 10 as associated with the recipe, and then the scanning area of the electron beam is finely adjusted so that the both images just overlaps with each other. The positioned wafer 5 is inspected for a pre-specified inspection area as to whether or not there is a defect in the pattern (step S6). For the pattern defect inspection, the aforementioned vector scan method and pattern defect detection means are used.

Such inspection data as a coordinate position of a pattern defect part and an image thereof are registered in the computer/controller 18. Further, when a reference image therefor is also stored in the image file, reviewing operation after the inspection can be facilitated.

In this manner, inspection of a sheet of the wafer is completed. When there are a plurality of wafers to be inspected still remaining in the wafer cassette, the next wafer is extracted from the wafer cassette and then repetitively subjected to the aforementioned inspecting operations according to the procedure of FIG. 6.

The reference image may be previously registered prior to the inspecting operations or may be newly registered or re-registered in the inspecting operations. For example, the image of the same pattern part in the just-previously inspected chip or cell can be repetitively re-registered as a reference image in the inspecting operations. As the reference image, pattern design information can be used in place of the sample image.

In the case where such a charged particle beam as an electron beam or an ion beam is used, with respect to such an sample that it takes a considerable time before its charge-up (charge accumulation on an insulator surface caused by the irradiation of the charged particle beam) is saturated, the charged particle beam may be irradiated for a predetermined period of time and then the sample image may be captured.

Although an X-Y stage has been used in the above embodiment, the X-Y stage may be replaced by an X-Y-T stage (T meaning tilt) to perform the pattern defect inspection under such a condition that a sample is tilted.

Only the pattern defect inspection has been explained above. However, when an abnormality is recognized in the inspection result, such analysis function as is done in a characteristic X-ray analyzer or an Auger electron analyzer may be attached as necessary so that analyzed data of the defect part can be also acquired.

Though an electron beam has been employed for image formation in the above embodiment, the electron beam may be replaced by an ion beam, an optical beam or a mechanical probe.

The above explanation has been made in connection with the case of one probe and one pixel, but the image formation may be carried out based on multi-probes and multi-pixels.

The above explanation has been made in connection with the case where a semiconductor wafer is observed in the foregoing embodiment, but the semiconductor wafer may be replaced by an image pick-up element, display element wafer or a sample of any shape other than the wafer.

It will be appreciated from the above explanation that compatibility can be realized between the pattern defect inspection with a high sensitivity and the high speed inspection with less-erroneous information.

In accordance with the foregoing embodiment of the present invention, there is provided a pattern defect inspecting apparatus which can suitably perform pattern defect inspection with a high sensitivity at a high speed while avoiding an increase of error detection rate.

What is claimed is:

1. A pattern defect inspecting apparatus for scanning a surface of a sample to be inspected with use of a predetermined probe and for inspecting a defect in a contoured pattern formed on the sample to be inspected on the basis of information on the pattern obtained by the scanning, wherein the only region of the sample surface to be scanned by said probe is a predetermined outer periphery region along the contour of said pattern formed on the sample, including the edge of the pattern.

2. A pattern defect inspecting apparatus as set forth in claim 1, wherein an image of said inspection sample including said scanned region is formed, a reference image associated with the sample image is previously registered in said inspecting apparatus, said sample image is compared with said previously registered reference image to find a difference between the images, and said image difference is detected as a defect in said pattern.

3. A pattern defect inspecting apparatus as set forth in claim 2, wherein a portion of the pattern of said sample image located out of a pre-determined prescribed range is detected as a pattern defect.

4. A pattern defect inspecting apparatus as set forth in claim 2, wherein image parameters of said sample image and reference image respectively are able to be independently modified.

5. A pattern defect inspecting apparatus as set forth in claim 2, wherein said sample image is an image obtained after irradiation of a beam on said sample for a predetermined period of time with use of a probe.

6. A pattern defect inspecting apparatus as set forth in claim 1, wherein, said sample is pre-aligned to form a reference image for alignment of a pre-registered sample and an alignment image corresponding to said reference image for alignment, and carrying out alignment of said sample by collating said reference image for alignment and said alignment image.

7. A pattern defect inspecting apparatus as set forth in claim 1, wherein said inspecting includes registering operational information for carrying out an inspection operation predeterminedly, reading sample information formed on said sample, reading out said operational information based on said read out sample information, and carrying out said inspection operation based on said read out operational information.

8. A pattern defect inspecting apparatus as set forth in claim 1, wherein an image for positioning said pattern reference is previously registered in said defect inspecting apparatus, an image of a positioning pattern formed on said sample is formed as associated with said positioning pattern reference image, and said positioning pattern image is collated with said positioning pattern reference image to achieve positioning of said sample.

9. A pattern defect inspecting apparatus as set forth in claim 1, wherein a line profile of said pattern is formed, a reference line profile is previously registered in said inspecting apparatus as associated with said line profile, said line profile is compared with said previously registered reference line profile to find a difference between both profiles, and said profile difference is detected as a pattern defect.

10. A pattern defect inspecting apparatus as set forth in claim 9, wherein said line profile is obtained after irradiation of a beam on said sample for a predetermined period of time with use of a probe.

11. A pattern defect inspecting apparatus as set forth in claim 9, wherein said line profile is obtained after irradiation of a beam on said sample for a predetermined period of time with use of a probe.

12. A pattern defect inspecting apparatus for scanning a surface of a sample to be inspected with use of a predetermined probe and for inspecting a defect in a contoured pattern formed on the sample to be inspected on the basis of information on the pattern obtained by scanning, wherein the only region of the sample surface to be scanned by said probe is within the pattern formed on the sample, and a predetermined outer periphery region alone the contour of said pattern formed on the sample, including the edge of the pattern.

13. A pattern defect inspecting apparatus as set forth in claim 12, wherein an image of said inspection sample including said scanned region is formed, a reference image associated with the sample image is previously registered in said inspecting apparatus, said sample image is compared with said previously registered reference image to find a difference between the images, and said image difference is detected as a defect in said pattern.

14. A pattern defect inspecting apparatus as set forth in claim 12, wherein a portion of the pattern of said sample image located out of a pre-determined prescribed range is detected as a pattern defect.

15. A pattern defect inspecting apparatus as set forth in claim 12, wherein image parameters of said sample image and reference image respectively are able to be independently modified.

16. A pattern defect inspecting apparatus as set forth in claim 12, wherein said sample image is an image obtained after irradiation of a beam on said sample for a predetermined period of time with use of a probe.

17. A pattern defect inspecting apparatus as set forth in claim 12, wherein, said sample is pre-aligned to form a reference image for alignment of a pre-registered sample and an alignment image corresponding to said reference image for alignment, and carrying out alignment of sample by collating said reference image for alignment sand said alignment image.

18. A pattern defect inspecting apparatus as set forth in claim 12, wherein said inspecting includes registering operational information for carrying out an inspection operation predeterminedly, reading sample information formed on said sample, reading out said operational information based on said read out sample information, and carrying out said inspection operation based on said read out operational information.

19. A pattern defect inspecting apparatus as set forth in claim 12, wherein an image for positioning pattern reference is previously registered in said defect inspecting apparatus, an image of a positioning pattern formed on said sample is formed as associated with said positioning pattern reference image, said positioning pattern image is collated with said positioning pattern reference image to achieve positioning of said sample.

20. A pattern defect inspecting apparatus as set forth in claim 12, wherein a line profile of said pattern is formed, a reference line profile is previously registered in said inspecting apparatus as associated with said line profile, said line profile is compared with said previously registered reference line profile to find a difference between both profiles, and said profile difference is detected as a pattern defect.

21. A pattern defect inspecting apparatus as set forth in claim 12, wherein said line profile is obtained after irradiation of a beam on said sample for a predetermined period of time with use of a probe.

22. A pattern defect inspecting apparatus as set forth in claim 12, wherein said line profile is obtained after irradiation of a beam on said sample for a predetermined period of time with use of a probe.

23. A pattern defect inspecting apparatus for scanning a surface of a sample to be inspected with use of a predetermined probe and for inspecting a defect in a contoured pattern formed on the sample to be inspected on the basis of information on the pattern obtained by scanning, wherein the only region of said sample surface to be scanned by said probe is a predetermined inner periphery region and a predetermined outer periphery region along the contour of said pattern formed on the sample, including the edge of the pattern.

24. A pattern defect inspecting apparatus as set forth in claim 23, wherein an image of said inspection sample including said scanned region is formed, a reference image associated with the sample image is previously registered in said inspecting apparatus, said sample image is compared with said previously registered reference image to find a difference between the images, and said image difference is detected as a defect in said pattern.

25. A pattern defect inspecting apparatus as set forth in claim 23, wherein a portion of the pattern of said sample image located out of a pre-determined prescribed range is detected as a pattern defect.

26. A pattern defect inspecting apparatus as set forth in claim 23, wherein image parameters of said sample image and reference image respectively are able to be independently modified.

27. A pattern defect inspecting apparatus as set forth in claim 23, wherein said sample image is an image obtained after irradiation of a beam on said sample for a predetermined period of time with use of a probe.

28. A pattern defect inspecting apparatus as set forth in claim 23, wherein, said sample is pre-aligned to form a reference image for alignment of a pre-registered sample and an alignment image corresponding to said reference image for alignment, and carrying out alignment of sample by collating said reference image for alignment sand said alignment image.

29. A pattern defect inspecting apparatus as set forth in claim 23, wherein said inspecting includes registering operational information for carrying out an inspection operation predeterminedly, reading sample information formed on said sample, reading out said operational information based on said read out sample information, and carrying out said inspection operation based on said read out operational information.

30. A pattern defect inspecting apparatus as set forth in claim 23, wherein an image for positioning pattern reference is previously registered in said defect inspecting apparatus, an image of a positioning pattern formed on said sample is formed as associated with said positioning pattern reference image, said positioning pattern image is collated with said positioning pattern reference image to achieve positioning of said sample.

31. A pattern defect inspecting apparatus as set forth in claim 23, wherein a line profile of said pattern is formed, a reference line profile is previously registered in said inspecting apparatus as associated with said line profile, said line profile is compared with said previously registered reference line profile to find a difference between both profiles, and said profile difference is detected as a pattern defect.

32. A pattern defect inspecting apparatus as set forth in claim 23, wherein said line profile is obtained after irradiation of a beam on said sample for a predetermined period of time with use of a probe.

33. A pattern defect inspecting apparatus as set forth in claim 23, wherein said line profile is obtained after irradiation of a beam on said sample for a predetermined period of time with use of a probe.

* * * * *